(12) United States Patent
Hui et al.

(10) Patent No.: US 11,241,448 B2
(45) Date of Patent: Feb. 8, 2022

(54) METHODS FOR CANCER THERAPY

(71) Applicant: Millennium Pharmaceuticals, Inc., Cambridge, MA (US)

(72) Inventors: Ai-Min Hui, Lexington, MA (US); Richard Labotka, Des Plaines, IL (US); Neeraj Gupta, Newton, MA (US); Karthik Venkatakrishnan, Cambridge, MA (US); Guohui Liu, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/188,492

(22) Filed: Mar. 1, 2021

(65) Prior Publication Data

US 2021/0177871 A1 Jun. 17, 2021

Related U.S. Application Data

(63) Continuation of application No. 17/000,907, filed on Aug. 24, 2020, now abandoned, which is a continuation of application No. 16/781,432, filed on Feb. 4, 2020, now abandoned, which is a continuation of application No. 16/517,963, filed on Jul. 22, 2019, now abandoned, which is a continuation of application No. 16/229,524, filed on Dec. 21, 2018, now abandoned, which is a continuation of application No. 14/716,761, filed on May 19, 2015, now abandoned.

(60) Provisional application No. 62/000,991, filed on May 20, 2014, provisional application No. 62/019,600, filed on Jul. 1, 2014, provisional application No. 62/088,154, filed on Dec. 5, 2014.

(51) Int. Cl.
| | | |
|---|---|---|
| *A61K 31/69* | (2006.01) | |
| *A61K 9/48* | (2006.01) | |
| *A61K 38/05* | (2006.01) | |
| *A61K 38/06* | (2006.01) | |
| *A61K 38/07* | (2006.01) | |
| *A61K 31/145* | (2006.01) | |
| *A61K 31/198* | (2006.01) | |
| *A61K 31/353* | (2006.01) | |
| *A61K 31/407* | (2006.01) | |
| *A61K 31/426* | (2006.01) | |
| *A61K 31/454* | (2006.01) | |

(52) U.S. Cl.
CPC ............ *A61K 31/69* (2013.01); *A61K 9/485* (2013.01); *A61K 9/4858* (2013.01); *A61K 9/4866* (2013.01); *A61K 31/145* (2013.01); *A61K 31/198* (2013.01); *A61K 31/353* (2013.01); *A61K 31/407* (2013.01); *A61K 31/426* (2013.01); *A61K 31/454* (2013.01); *A61K 38/05* (2013.01); *A61K 38/06* (2013.01); *A61K 38/07* (2013.01)

(58) Field of Classification Search
CPC ...... A61K 31/69; A61K 9/485; A61K 9/4858; A61K 9/4866
See application file for complete search history.

(56) References Cited

U.S. PATENT DOCUMENTS

| | | | |
|---|---|---|---|
| 2,160,413 | A | 5/1939 | Dohrn et al. |
| 4,499,082 | A | 2/1985 | Shenvi et al. |
| 5,106,948 | A | 4/1992 | Kinder et al. |
| 5,159,060 | A | 10/1992 | Kinder et al. |
| 5,169,841 | A | 12/1992 | Kleeman et al. |
| 5,187,157 | A | 2/1993 | Kettner et al. |
| 5,242,904 | A | 9/1993 | Kettner et al. |
| 5,250,720 | A | 10/1993 | Kettner et al. |
| 5,492,900 | A | 2/1996 | Lahann |
| 5,574,017 | A | 11/1996 | Gutheil |
| 5,580,486 | A | 12/1996 | Labeque et al. |
| 5,780,454 | A | 7/1998 | Adams et al. |
| 5,834,487 | A | 11/1998 | Lum et al. |
| 5,837,531 | A | 11/1998 | Dedieu et al. |
| 5,935,944 | A | 8/1999 | Lahann |
| 5,990,083 | A | 11/1999 | Iqbal et al. |

(Continued)

FOREIGN PATENT DOCUMENTS

| | | |
|---|---|---|
| AU | 3951389 A | 3/1990 |
| EP | 0354522 A1 | 2/1990 |

(Continued)

OTHER PUBLICATIONS

Andersen, M.W. et al., "E- and Z-Pentenylboronates, Reagents for Simple Diasteroselection on Addition to Aldehydes," Chemische Berichte, vol. 122, (1989), pp. 1777-1782.

(Continued)

*Primary Examiner* — Genevieve S Alley
(74) *Attorney, Agent, or Firm* — Honigman LLP; Lucy X. Yang; Jonathan P. O'Brien

(57) ABSTRACT

The present disclosure relates to methods or dosing regimens comprising a proteasome inhibitor of formula (I), or a pharmaceutically acceptable salt thereof,

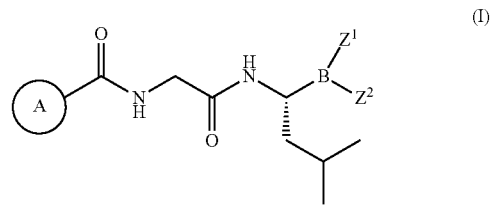

(I)

for treating cancer, or preventing cancer recurrence or progression; wherein ring A, $Z^1$ and $Z^2$ are as defined herein.

23 Claims, 2 Drawing Sheets

(56) References Cited

U.S. PATENT DOCUMENTS

| | | | |
|---|---|---|---|
| 6,060,462 | A | 5/2000 | Galemmo, Jr. et al. |
| 6,066,730 | A | 5/2000 | Adams et al. |
| 6,083,903 | A | 7/2000 | Adams et al. |
| 6,169,076 | B1 | 1/2001 | Shull et al. |
| 6,297,217 | B1 | 10/2001 | Adams et al. |
| 6,699,835 | B2 | 3/2004 | Plamondon et al. |
| 6,713,446 | B2 | 3/2004 | Gupta |
| 6,781,000 | B1 | 8/2004 | Wang et al. |
| 6,846,806 | B2 | 1/2005 | Priestley |
| 6,958,319 | B2 | 10/2005 | Gupta |
| 7,109,323 | B2 | 9/2006 | Plamondon et al. |
| 7,223,745 | B2 | 5/2007 | Chatterjee et al. |
| 7,442,830 | B1 | 10/2008 | Olhava et al. |
| 7,687,662 | B2 | 3/2010 | Olhava et al. |
| 7,799,782 | B2 | 9/2010 | Munson et al. |
| 8,003,819 | B2 | 8/2011 | Olhava et al. |
| 8,859,504 | B2 | 10/2014 | Elliott et al. |
| 2002/0169114 | A1 | 11/2002 | Gupta |
| 2002/0188100 | A1 | 12/2002 | Plamondon et al. |
| 2004/0171556 | A1 | 9/2004 | Purandare et al. |
| 2005/0107307 | A1 | 5/2005 | Bernadini et al. |
| 2005/0282742 | A1 | 12/2005 | Plamondon et al. |
| 2006/0084592 | A1 | 4/2006 | Boucher |
| 2006/0252740 | A1 | 11/2006 | Johnson et al. |
| 2007/0185060 | A1 | 8/2007 | Wang |
| 2009/0325903 | A1 | 12/2009 | Elliott et al. |
| 2010/0081633 | A1 | 4/2010 | Fleming et al. |
| 2010/0204180 | A1 | 8/2010 | Olhava et al. |
| 2011/0245203 | A1 | 10/2011 | Fleming et al. |
| 2012/0041196 | A1 | 2/2012 | Bernardini et al. |

FOREIGN PATENT DOCUMENTS

| | | | |
|---|---|---|---|
| EP | 0092999 | B1 | 4/1992 |
| JP | 62033170 | A | 2/1987 |
| JP | 63230682 | A | 9/1988 |
| JP | 63258446 | A | 10/1988 |
| JP | 2002145848 | A | 5/2002 |
| JP | 2011-524903 | A | 9/2011 |
| WO | 1993010127 | A1 | 5/1993 |
| WO | 1994004542 | A1 | 3/1994 |
| WO | 1994004653 | A1 | 3/1994 |
| WO | 1996013266 | A1 | 5/1996 |
| WO | 1996014857 | A1 | 5/1996 |
| WO | 1998035691 | A1 | 8/1998 |
| WO | 1999015183 | A1 | 4/1999 |
| WO | 1999030707 | A1 | 6/1999 |
| WO | 2000024392 | A1 | 5/2000 |
| WO | 2000057887 | A1 | 10/2000 |
| WO | 2001002424 | A2 | 1/2001 |
| WO | 2002005923 | A1 | 1/2002 |
| WO | 2002059130 | A1 | 8/2002 |
| WO | 2002059131 | A1 | 8/2002 |
| WO | 2002096933 | A1 | 12/2002 |
| WO | 2003033506 | A1 | 4/2003 |
| WO | 2003033507 | A1 | 4/2003 |
| WO | 2003059898 | A2 | 7/2003 |
| WO | 2003105860 | A1 | 12/2003 |
| WO | 2004064755 | A2 | 8/2004 |
| WO | 2005016859 | A2 | 2/2005 |
| WO | 2005021558 | A2 | 3/2005 |
| WO | 2005097809 | A2 | 10/2005 |
| WO | 2005111008 | A2 | 11/2005 |
| WO | 2006052733 | A1 | 5/2006 |
| WO | 2006086600 | A1 | 8/2006 |
| WO | 2007005991 | A1 | 1/2007 |
| WO | 2007089618 | A2 | 8/2007 |
| WO | 2008027273 | A2 | 3/2008 |
| WO | 2009006473 | A2 | 1/2009 |
| WO | 2009020448 | A1 | 2/2009 |
| WO | 2009154737 | A1 | 12/2009 |
| WO | 2010036357 | A1 | 4/2010 |
| WO | 2011123502 | A1 | 10/2011 |

OTHER PUBLICATIONS

Armstrong, T., et al., "Central Nervous System Toxicity from Cancer Treatment," Current Oncology Reports, vol. 5, (2004), pp. 11-19.
Bartusek, M., et al., "Boron chelates with citrate," Scripta-Chemistry, vol. 21 (1991) pp. 63-66.
Berge, et al., J. Pharm. Sci., 1977, vol. 66, 1-19.
Bosch, L.I., et al., "Binary and ternary phenylboronic acid complexes with saccharides and Lewis bases," Tetrahedron, 2004, 60, pp. 11175-11190.
Brittain's publication, "Crystalline and Pharmaceutical Composition," 1999, pp. 348-361.
Cancer [online], Retrieved on Jul. 6, 2007: MedlinePlus, a service of Medicine and the National Institutes of Health, Retrieved from the Internet, URL: http://www.nlm.nih.gov/medlineplus/cancer.html, 10 pages.
Capitulo 28: Iiofilizacion, Farmacotecnia: teoria y practicatomo 3, 1982, MX, pp. 1038-1041.
Ciechanover, A., "The Ubiquitin-Proteasome Proteolytic Pathway," Cell, vol. 79 (Oct. 7, 1994), pp. 13-21.
Decision T 428/12 (Datasheet for the decision of Jun. 26, 2014 EP1660507 Opposition).
Dick, L.R., et al., "Building on bortezomib: second-generation proteasome inhibitors as anti-cancer therapy", Elsevier, Drug Discovery Today, vol. 15, No. 5, Mar. 6, 2010, pp. 243-249.
Dootz, H., "Rote Liste 2006", entry 86130.
EP09767050.9 Communication pursuant to Article 94(3) EPC (Examination Report) dated Oct. 25, 2011 from corresponding European patent application 09 767 050.9-2117.
EP1660507 Opponent's Notice of Opposition dated May 4, 2010, 26 pages.
EP1660507 Proprietor's Response to the Notice of Opposition with Amended Claims dated Jan. 17, 2011, 61 pages.
EP1660507 Summons to Attend Oral Proceedings with Annex dated Apr. 1, 2011, 11 pages.
EP1660507 Proprietor's Submissions and Amendments dated Sep. 7, 2011, 122 pages.
EP1660507 Opponent's Reply to Proprietor's Sep. 5, 2011 Submission dated Sep. 19, 2011, 23 pages.
EP1660507 Proprietor's Letters Regarding Oral Proceedings dated Sep. 21, 2011, 9 pages.
EP2178888 Summons to Attend Oral Proceedings with Annex, filed Oct. 17, 2011, cited by Cephalon as D6 in Opposition filed against EP2178888, 3 pages.
EP1660507 Oral Proceedings Minutes and Results dated Nov. 2, 2011, 59 pages.
EP1660507 Opponent's Request for Correction of Minutes of Oral Proceedings dated Nov. 10, 2011, 3 pages.
EP1660507 Proprietor's Request Regarding Minutes of Oral Proceedings dated Nov. 29, 2011, 3 pages.
EP1660507 Correction of Minutes of Oral Proceedings dated Dec. 5, 2011, 3 pages.
EP1660507 Annex filed Dec. 7, 2011, to Opposition Letter Dated Nov. 2, 2011, 2 pages.
EP1660507 Opponent's Letter filed Dec. 7, 2011, Further to Proprietor's Representative's Letter Dated Nov. 29, 2011, 3 pages.
EP1660507 Interlocutory Decision in Opposition Proceedings dated Dec. 14, 2011, 263 pages.
EP2178888 Annex to Applicant's letter filed during examination dated Dec. 30, 2011, filed Dec. 30, 2011, cited by Celphalon as D8 in Opposition filed against EP2178888, 3 pages.
EP2178888, Applicant's letter filed during examination, filed Dec. 30, 2011, cited by Celphalon as D7 in Opposition filed against EP2178888, 3 pages.
EP1660507 Opponent's Notice of Appeal Against Decision of the Opposition Division dated Feb. 23, 2012, 5 pages.
EP1660507 Proprietor's Notice of Appeal Against Decision of the Opposition Division dated Feb. 23, 2012, 2 pages.
EP1660507 Opponent's Statement of Grounds of Appeal dated Apr. 23, 2012, 38 pages.

(56) References Cited

OTHER PUBLICATIONS

EP1660507 Proprietor's Submissions and Amendments dated Apr. 24, 2012, 189 pages.
EP1660507 Opponent's Reply filed Sep. 12, 2012, to Proprietor's Grounds of Appeal of Apr. 24, 2012, 13 pages.
EP1660507 Proprietor's Response to Opponent's Grounds of Appeal dated Sep. 12, 2012, 498 pages.
EP1660507 Proprietor's letter filed during the oral proceedings filed Jan. 11, 2013, cited by Cephalon as D14 in Opposition filed against EP2178888, 10 pages.
EP2178888 Opposition, Opponent's Notice of Opposition, filed Apr. 4, 2013, 25 pages.
Gardner, R.C., et al., "Characterization of peptidyl boronic acid inhibitors of mammalian 20 S and 26 S proteasomes and their inhibition of proteasomes in cultured cells," Biochemistry, vol. 346 (2000) pp. 447-454.
Gennaro, A.R. (editor), "Remington: The science and practice of pharmacy,"20th Edition, Chapter 42, Lippincott Williams & Wilkins (publishers), Baltimore, MD (2000) pp. 802-803.
Golub, T.R., et al., "Molecular Classification of Cancer: Class Discovery and Class Prediction by Gene Expression Monitoring," Science, vol. 286, pp. 531-537 (Oct. 15, 1999).
Gray, C.W., "Boronic acid receptors for a-hydroxycarboxylates: high affinity of Shinkai's glucose receptor for tartrate," Journal of Organic Chemistry, vol. 67, No. 15 (2002) pp. 5426-5428.
Greene, T.W., et al., "Protective groups in organic synthesis," John Wiley & Sons, Inc., Editor (1999) Third Edition, pp. 531-537.
Groll, M., et al., "Structure of 20S Proteasome from Yeast at 2.4A Resolution", Nature, vol. 386 (Apr. 3, 1997), pp. 463-471.
Gross, E., et al., "The Peptides: Analysis, Synthesis, Biology," Protection of Functional Groups in Peptide Synthesis, vol. 3, (Academic Press New York) (1981), pp. 3-88.
Hall, Denis G., "Boronic Acids: Preparation, Applications in Organic Synthesis and Medicine," Wiley-VCH, 2005, pp. 1-99.
Harris, J.L., et al., "Substrate Specificity of the Human Proteasome," Chemistry & Biology, vol. 8 (2001), pp. 1131-1141.
Hoffmann, R.W. et al., "Towards an Understanding of Cram/anti-Cram Selectivity on Addition of Crotylboronates to a-Methylbutyraldehyde," Chemische Berichte, vol. 123, (1990), pp. 2387-2394.
Houston, T.A., et al., "Boric acid catalyzed chemoselective esterification of a-hydroxycarboxylic acids," Organic Letters, vol. 6, No. 5 (2004) pp. 679-681.
http://goldbook.iupac.org/A00228.html. Retrieved from IUPAC, Compendium of Chemical Terminology, 2nd ed. (the "Gold Book"). Compiled by A. D. McNaught and A. Wilkinson, Blackwell Scientific Publications, Oxford (1997), XML on-line corrected version: http://goldbook.iupac.org (2006-) created by M. Nic, J. Jirat, B. Kosata; updates compiled by A. Jenkins. I SBN 0-9678550-9-8. doi:10.1351/goldbook, 1 page.
International Search Report and Written Opinion for PCT/US2007/017440 dated Dec. 3, 2007, 3 pages.
International Search Report for PCT/US2009/003602 dated Oct. 5, 2009, 2 pages.
International Search Report for PCT/US2009/005324 dated Jan. 19, 2010, 2 pages.
International Search Report for PCT/US2011/030455 dated Jun. 7, 2011, 1 pages.
JP4738426 Publication for Opposition, dated Sep. 28, 1972.
Kataoka, K., et al., "Totally synthetic polymer gels responding to external glucose concentration: their preparation and application to on-off regulation of insulin release," Journal of the American Chemical Society, vol. 120 (1998) pp. 12694-12695.
Kettner, C.A. et al., "Inhibition of the Serine Proteases Leukocyte Elastase, Pancreatic Elastase, Cathepsin G, and Chymotrypsin by Peptide Boronic Acids," The Journal of Biological Chemistry, vol. 259, No. 24, (Dec. 25, 1984), pp. 15106-15114.
Kibbe, A.H. (editor), "Handbook of Pharmaceutical Excipients," 3rd Edition, American Pharmaceutical Association (publishers), Washington, D.C. (2000) pp. 324-328.

Kinder, D.H., et al., "Acylamino boronic acids and difluoroborane analogues of amino acids: potent inhibitors of chymotrypsin and elastase," Journal of Medicinal Chemistry, vol. 28, No. 12 (1985) pp. 1917-1925.
King, R.W., et al., "How Proteolysis Drives the Cell Cycle," Science, vol. 274 (Dec. 6, 1996), pp. 1652-1659.
Kisselev, A.F., et al., "Proteasome inhibitors: from research tools to drug candidates," Chemistry & Biology, vol. 8, No. 8 (2001) pp. 739-758.
Korcek, S., et al., "Absolute rate constants for the autoxidation of organometallic compounds. Part II. Benzylboranes and 1-phenylethylboranes," Journal of the Chemical Society, Perkin Transaction 2, (1972) pp. 242-248.
Kupperman, E., et al., "Evaluation of the Proteasome Inhibitor MLN9708 in Preclinical Models of Human Cancer," Cancer Research, vol. 70, No. 5, Mar. 1, 2010, pp. 1970-1980.
Lala, P.K. et al., "Role of Nitric Oxide in Tumor Progression: Lessons from Experimental Tumors," Cancer and Metastasis Reviews, vol. 17, pp. 91-106 (1998).
Lieberman, H., et al., "Tablet formulation and design." Pharmaceutical Dosage Forms: tablets vol. 1, 1989, US, pp. 91-127.
Loidl, G., et al., "Bifunctional inhibitors of the trypsin-like activity of eukaryotic proteasomes," Chemistry & Biology, vol. 6, No. 4 (1999) pp. 197-204.
Lorand, J.P., et al., "Polyol complexes and structure of the benzeneboronate ion," Journal of Organic Chemistry, vol. 24 (1958) pp. 769-774.
Matteson, D.S., et al., "99% Chirally Selective Syntheses via Pinanediol Boronic Esters: Insect Pheromones, Diols, and an Amino Alcohol," Journal of American Chemical Society, vol. 108, No. 4, 1986, pp. 810-819.
Meiland, M., et al., "Seven-membered ring boronates at trans-diol moieties of carbohydrates," Tetrahedron Letters, vol. 50 (2009) pp. 469-472.
Millennium Pharmaceuticals, Inc., "Highlights of prescribing information Ninlaro," revised Nov. 2015.
Mullard, A., "Next-generation proteasome blockers promise safer cancer therapy", Nature Medicine, vol. 18 No. 1, Jan. 2012, p. 7.
Nalepa, G., et al., "Drug discovery in the ubiquitin-proteasome system" Nature Reviews Drug Discovery 2006, 5, 596-613.
Palombella, V.J., et al., "The Ubiquitin-Proteasome Pathway Is Required for Processing the NF-x131 Precursor Protein and the Activation of NF-KB," Cell, vol. 78, (Sep. 9, 1994), pp. 773-785.
Prasad S., et al., "Studies on the formation of some borocitrates," Journal of the Indian Chemistry Society, vol. 44, No. 3 (1967) pp. 219-220.
Richardson, P.G., et al., "A phase 2 study of bortezomib in relapsed, refractory myeloma," The New England Journal of Medicine, vol. 348, No. 26 (Jun. 26, 2003) pp. 2609-2617.
Rowe, R. C., et al., "Handbook of Pharmaceutical Excipients", Pharmaceutical Press and American Pharmacists Association, Ed. 5 (2006), 185-187.
Ruggeri, B., "The Development and Pharmacology of Proteasome Inhibitors for the Management and Treatment of Cancer," Advances in Pharmacology, vol. 57, 2009, pp. 91-135.
Scheibe, E., "The borocitrates and their preparation," The Pharmaceutical Journal and Transactions, Third Series, No. 542 (Nov. 18, 1880) p. 389.
Scientific discussion for the approval of Velcade, EMEA 2004, pp. 1-42.
Snyder, H.R., et al., "Aryl boronic acids, II. Aryl boronic anhydrides and their amine complexes," Journal of the American Chemical Society, vol. 80 (Jul. 20, 1958) pp. 3611-3615.
Stella, V.J., et al., "Development of parenteral formulations of experimental cytotoxic agents. I. Rhizoxin (NSC-332598),"International Journal of Pharmaceutics, vol. 43 (1988) pp. 191-199.
Tran, T., et al., "Synthesis and structure-activity relationship of N-acyl-Gly-, N-acyl-Sar- and N-blocked¬ boroPro inhibitors of FAP, DPP4, and POP," Bioorganic & Medicinal Chemistry Letters, vol. 17 (2007) pp. 1438-1442.
United States District Court of Delaware, "*Millennium Pharmaceuticals Inc. v. Sandoz Inc.*, Dec. 1011, U.S. District Court, District of Delaware (Wilmington 2015)".

(56) References Cited

OTHER PUBLICATIONS

U.S. Appl. No. 13/249,738: Office Action (made final) dated Sep. 7, 2012 in U.S. Appl. No. 13/249,738, 15 pages.
U.S. Appl. No. 13/249,738: Office Action dated Mar. 7, 2012 in U.S. Appl. No. 13/249,738 (EPO date Mar. 7, 2012), 62 pages.
U.S. Appl. No. 13/249,739: Response Filed Jul. 9, 2012 to Mar. 7, 2012 Office Action in U.S. Appl. No. 13/249,739, 9 pages.
University of the Sciences in Philadelphia, "Remington, The Science and Practice of Pharmacy", 21st Edition Chapter 67 p. 1341, published May 1, 2005.
Van Duin, M., et al., "Studies on borate esters I," Tetrahedron, vol. 40, No. 15 (1984) pp. 2901-2911.
Van Duin, M., et al., "Studies on borate esters II," Tetrahedron, vol. 41, No. 16 (1985) pp. 3411-3421.
Wallace, R.H. et al., "Preparation and 1-Carbon Homologation of Boronic Ester Substituted 02-isoxazolines: The 1,3 Dipolar Cycloadditon of Nitrile Oxides to Vinyl Boronic Esters," Tetrahedron Letters, vol. 33, No. 46, (1992), pp. 6941-6944.
Wang, Y. J., et al., "Parenteral Formulations of Proteins and Peptides: Stability and Stabilizers" Journal of Parenteral Science and Technology 1988, 42(supplement), S3-S26.
Williams, N.A., et al., "The effects of cooling rate on solid phase transitions and associated vial breakage occurring in frozen mannitol solutions," Journal of Parenteral Science & Technology, vol. 40, No. 4 (Jul.-Aug. 1986) pp. 135-141.
Williams, N.A., et al., "Vial breakage by frozen mannitol solutions: correlation with thermal characteristics and effect of stereoisomerism, additives, and vial configuration," Journal of Parenteral Science & Technology, vol. 45, No. 2 (Mar.-Apr. 1991) pp. 94-100.
Wiskur, Sheryl L. et al., "Thermodynamic Analysis of Receptors Based on Guanidinium/Boronic Acid Groups for the Complexation of Carboxylates, a-Hydroxycarboxylates, and Diols: Driving Force for Binding and Cooperativity", Chem. Eur. J. 2004, 10, 3792-3804.
Zenk, R., et al., "Organic Boronic Acids and Boronic Acid Esters in Industrial Synthesis," Chimica Oggi (Chemistry Today), (May 2003), pp. 70-73.
Attal, M., et al. "Lenalidomide Maintenance adter Stem-Cell Transplantation for Multiple Myeloma", The New England Journal of Medicine, 366, 19, (2012), pp. 1782-1791.
Cancer Consultants, "MLN9708 "Oral Velcade" Shows Promise in Multiple Myeloma", accessed at http://cancer.unm.edu/2013/01/03/mln9708-oral-velcade-shows-promise-in-multiple-myeloma/ Jun. 21, 2017.
EP2318419 Actavis Group PTC ehf Opposition dated Jan. 8, 2016, 14 pages.
EP2318419 Generics (U.K.) Limited Opposition dated Jan. 8, 2016, 44 pages.
EP2318419 Teva Pharmaceutical Industries Ltd. Opposition dated Jan. 8, 2016, 21 pages.
EP2318419 Proprietor's Notice of Oppositions dated Jan. 25, 2016, 3 pages.
EP2318419 EPO Invitation to Opponent to File an Authorisation dated Feb. 4, 2016, 1 page.
EP2318419 Opponent's Reply to Invitation to File an Authorisation dated Feb. 11, 2016, 2 pages.
EP2318419 Proprietor's Notice of Oppositions (R. 79(1) EPC) dated Feb. 16, 2016, 2 pages.
EP2318419 Opponent's Further Notice of Oppositions dated Feb. 16, 2016, 3 pages.
EP1355910 Decision of the Board of Appeal revoking EP1355910, Sep. 29, 2016, 39 pages.
EP1355910 Decision of the Opposition Division revoking EP1355910, May 6, 2014, 31 pages.
EP2730581 Communication of a Notice of Opposition, Feb. 6, 2017, 34 pages.
Ferrier, R.J., "Carbohydrate Boronates", Advances in Carbohydrate Chemistry and Biochemistry, 1978, vol. 35, pp. 31-80.
Hall, Denis G., "Boronic Acid-based Receptors and Sensors for Saccharides," Wiley-VCH, 2006, pp. 441-480.
Kumar, S. K., et al., "A Phase 1/2 Study of Weekly MLN9708, an Investigational Oral Proteasome Inhibitor, in Combination with Lenalidomide and Dexamethasone in Patients with Previously Untreated Multiple Myeloma (MM)", Blood Journal, vol. 120, Abstract 332 (2012), pp. 1-8.
Kumar, S. K., et al., "Weekly MLN9708, an investigational oral proteasome inhibitor, in relapsed/refractory multiple myeloma: Results from a phase I study after full enrollment", ASCO Annual Meeting 2013, Jun. 1, 2013, XP055204370.
Kumar, S. K., et al., "Phase 1 study of weekly dosing with the investigational oral proteasome inhibitor ixazomib in relapsed/refractory multiple myeloma", Blood, vol. 124, No. 7, Aug. 14, 2014, pp. 1047-1055, XP055204406.
Li, V., MLN9708, "Son of Velcade," Shows Promising Initial Results in Multiple Myeloma (ASH 2011), The Myeloma Beacon, Dec. 16, 2011, pp. 1-3.
Merlini, G., et al., "MLN9708, a novel, investigational oral proteasome inhibitor, in patients with relapsed or refractory light-chain amyloidosis: Results of a phase 1 study", 54th Annual Meeting of the American Society of Hematology (ASH), Dec. 1, 2012, XP055204440, Atlanta, GA, USA.
Merlini, G., et al., "Long-Term Outcome of a Phase 1 Study of the Investigational Oral Proteasome Inhibitor Ixazomib at the Recommended Phase 3 Dose in Patients with Relapsed or Refractory Systemic Light-Chain (AL) Amyloidosis", 56th ASH Annual Meeting and Exposition, Dec. 7, 2014, XP055204466, San Francisco, CA, USA.
NCT01718743, accessed at https://clinicaltrials.gov/archive/NCT01718743/ 2012_10_30, Jun. 21, 2017.
Pikal, M., "Freeze Drying", Encyclopedia of Pharmaceutical Technology, Marcel Dekker, New York, 1994, vol. 6, pp. 275-303.
Shah, Jatin. J., et al., "Phase II Study of the combination of MLN9708 with Lenalidomide as Maintenance Therapy post Autologous Stem Cell Transplant in Patients with Multiple Myeloma," ASH 2013 Annual Meeting Abstract 1983 Poster Presentation, (2013), downloaded from http://www.myelomabeacon.com/docs/ash2013/1983.pdf.
Sonneveld, P., et al., "Bortezomib Induction and Maintenance Treatment in Patients with Newly Diagnosed Multiple Myeloma: Reults fo the Randomized Phase III HOVON-65/GMMG-HD4 Trial", Journal of Clinical Oncology, vol. 30, No. 24, pp. 2946-2955 (2012).
Takeda Annual Report 2012, accessed at http://www.takeda.co.jp/investor-information/annual/pdf/index/ar2012_10jp.pdf.p.29, Sep. 16, 2016.
Wu, S., et al., "Degradation Pathways of a Peptide Boronic Acid Derivative, 2-Pyz-(CO)-Phe-Leu-B(OH)2", J. Pharm.Sci., 2000, 89(6), pp. 758-765.
Buac, Daniela, et al., "From Bortezomib to other Inhibitors of the Proteasome and Beyond," Current Pharmaceutical Design, May 17, 2013; 19(22); pp. 4025-4038.
Murakami, Hirokazu, et al., "Diagnosis and management guideline of multiple myeloma," Japanese Journal of Clinical Medicine, 2007; 65(12); pp. 2167-2176.
Takeda (China) Holdings Co., Ltd., "https://www.takeda.com/zh-cn/news-room/news-releases/2014/2014-1-22/," Jan. 22, 2014, downloaded on Dec. 18, 2018 (with English Translation of lines 19 to 20).

FIG. 1    Results of exposure-response analyses of safety and efficacy data
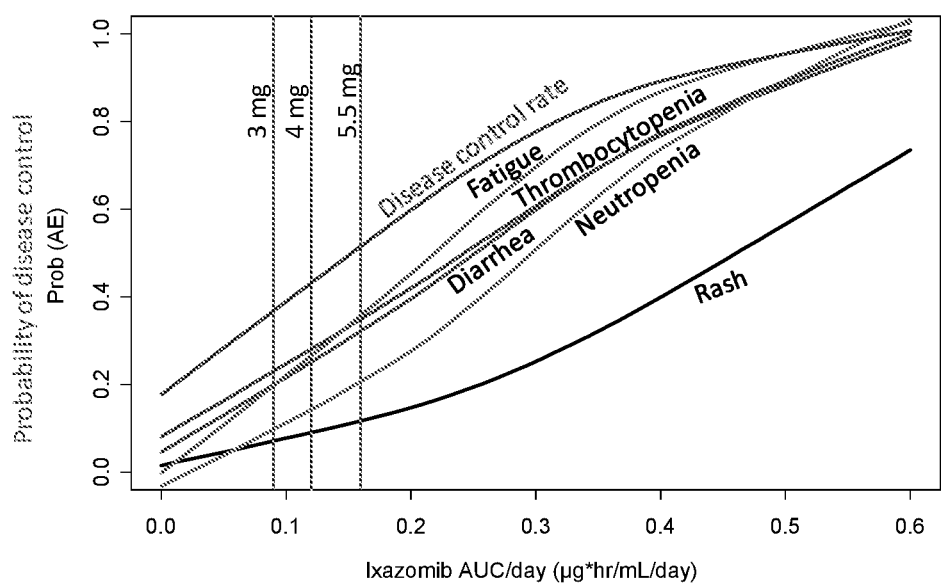

FIG. 2    Best overall response in 21 patients who received ixazomib maintenance therapy
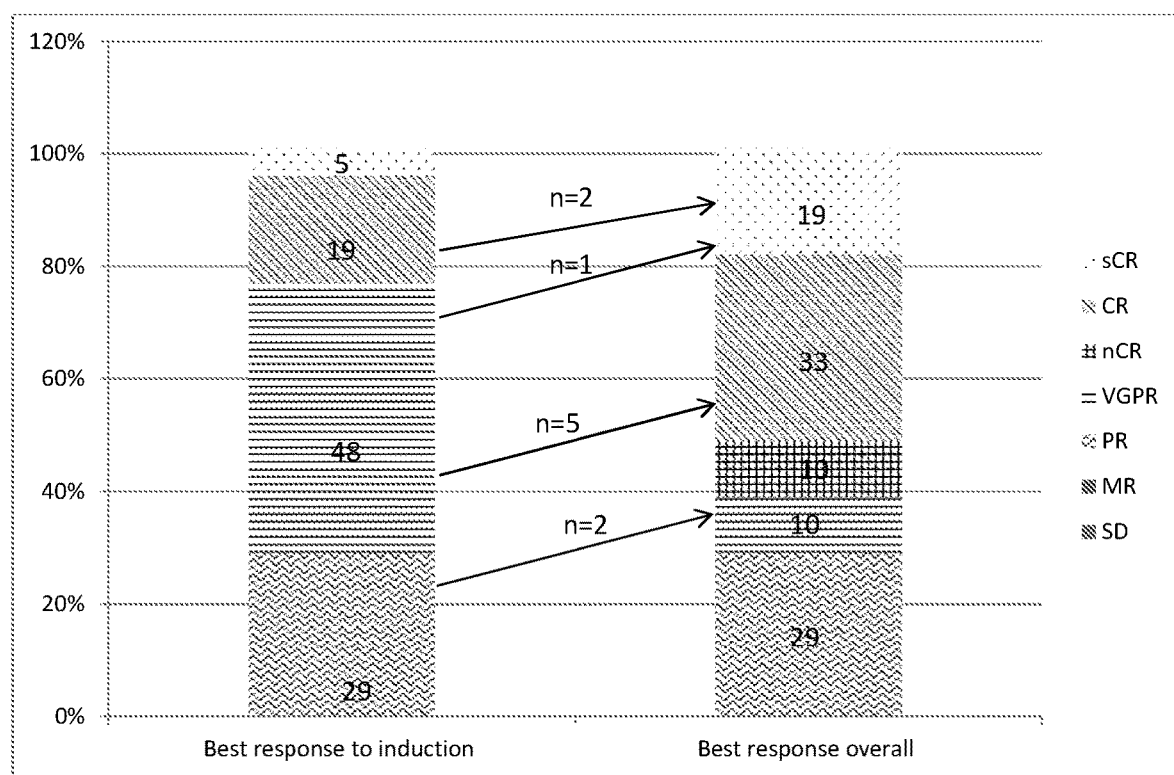

METHODS FOR CANCER THERAPY

PRIORITY CLAIM

Cross-Reference to Related Applications

This application is a continuation of U.S. application Ser. No. 17/000,907, filed Aug. 24, 2020, which is a continuation of U.S. application Ser. No. 16/781,432, filed Feb. 4, 2020, which is a continuation of U.S. application Ser. No. 16/517, 963, filed Jul. 22, 2019, which is a continuation of U.S. application Ser. No. 16/229,524, filed Dec. 21, 2018, which is a continuation of U.S. application Ser. No. 14/716,761, filed May 19, 2015, which claims priority to U.S. Provisional Application No. 62/000,991, filed May 20, 2014, U.S. Provisional Application No. 62/019,600, filed Jul. 1, 2014 and U.S. Provisional Application No. 62/088,154, filed Dec. 5, 2014. The entire contents of the aforementioned applications are incorporated herein by reference.

FIELD OF THE INVENTION

The present disclosure relates to methods or dosing regimens comprising proteasome inhibitors of formula (I) for treating cancer, or preventing cancer recurrence or progression.

BACKGROUND OF THE INVENTION

Cancer has a major impact on society in the United States and across the world. Cancer is the second most common cause of death in the US, exceeded only by heart disease, accounting for nearly 1 of every 4 deaths. The National Cancer Institute estimates that in 2015, approximately 1,658,370 new cases of cancer will be diagnosed in the United States and 589,430 people will die from the disease. Although medical advances have improved cancer survival rates, there is a continuing need for new and more effective treatment.

Multiple myeloma, a B-cell tumor of malignant plasma cells within the bone marrow, remains incurable despite advances in novel therapies with proteasome inhibitors (PIs), immunomodulating drugs (IMiD), and stem cell transplant (SCT) therapy. Multiple myeloma is characterized by the accumulation of plasma cells in the bone marrow (and other organs) and can result in bone marrow failure, bone destruction, hypercalcemia, and renal failure. It constitutes approximately 1% of all reported neoplasms and approximately 13% of hematologic cancers worldwide. In the Americas, Canada, and Western European countries, approximately five to seven new cases of multiple myeloma are diagnosed per 100,000 people each year. Palumbo and Anderson, *N Engl J Med* 2011; 364(11):1046-60; Landgren and Weiss, *Leukemia* 2009; 23(10):1691-7; Haroussean, et al., *Annals of Oncology* 2008; 19 Suppl 2:ii55-7. Although less common in Asian countries, incidences of multiple myeloma have increased almost 4-fold in the past 25 years and are characterized by younger age of onset, more invasive disease, and a less favorable prognosis (Huang, et al., Cancer 2007; 110(4):896-905; Qiu, et al., Clinical Epidemiological Study on Multiple Myeloma in China (ASH Annual Meeting Abstracts) 2008; 112(11):abstr 2723).

Multiple myeloma is sensitive to many cytotoxic drugs including alkylating agents, anthracyclines, and corticosteroids for both initial treatment and relapsed disease. Over the past decade, significant achievements have been made in expanding treatment options for multiple myeloma with novel therapies such as thalidomide, bortezomib, and lenalidomide. These regimens have extended progression-free survival (PFS) and/or time-to-progression (TTP) (Palumbo, et al., Leukemia 2008; 22(2):414-23; Mateos, et al., Journal of Clinical Oncology 2010; 28(13):2259-66; Gay, et al., Haematologica 2010; 94:0507; Richardson, et al., Hematology 2007: 317-23; Dimopoulos, et al., Leukemia 2009; 23(11):2147-52). The introduction of novel therapies and the increased use of high-dose therapy (HDT) significantly improved overall survival in patients with newly diagnosed multiple myeloma (NDMM) who were eligible for autologous stem cell transplant (ASCT) (Kumar, et al., Blood 2008; 111(5):2516-20; Brenner, et al., Blood 2008; 111(5):2521-6; Libby, et al., Declining myeloma mortality rates in the United States following introduction of novel therapies In: International Myeloma Workshop Paris, France; 2011).

Despite more therapeutic options, multiple myeloma remains incurable, and patients with early stage cancer remain at risk for relapse after their initial therapy. When patients relapse after their initial therapy, they demonstrate variable responses to subsequent treatments with decreasing likelihood and duration of response (DOR). Patients become refractory to approved therapies and ultimately are left with no alternative treatment options. There is a need for new and better drugs and regimens which improve patient survival rates and/or decrease recurrence of cancer following completion of primary treatment. The methods of the instant disclosure present cancer patients with new options.

SUMMARY OF THE INVENTION

The present disclosure provides methods or dosing regimens for treating cancer, or preventing cancer recurrence or progression. The methods or the dosage regimens comprise administering to a patient, who has undergone a primary cancer therapy, a compound of formula (I), or a pharmaceutically acceptable salt thereof,

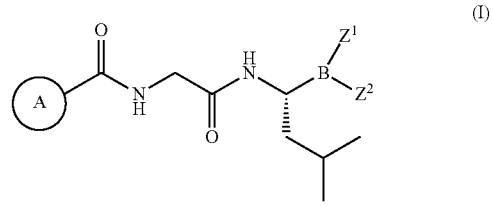

on a dosing schedule comprising at least four 28-day treatment cycles, wherein the 28-day treatment cycle comprises four consecutive weeks in which the compound of formula (I), or a pharmaceutically acceptable salt thereof, is administered once a week for the first three weeks of the treatment cycle and the compound of formula (I), or pharmaceutically acceptable salt thereof, is not administered during the fourth week, wherein ring A is

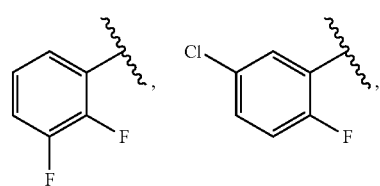

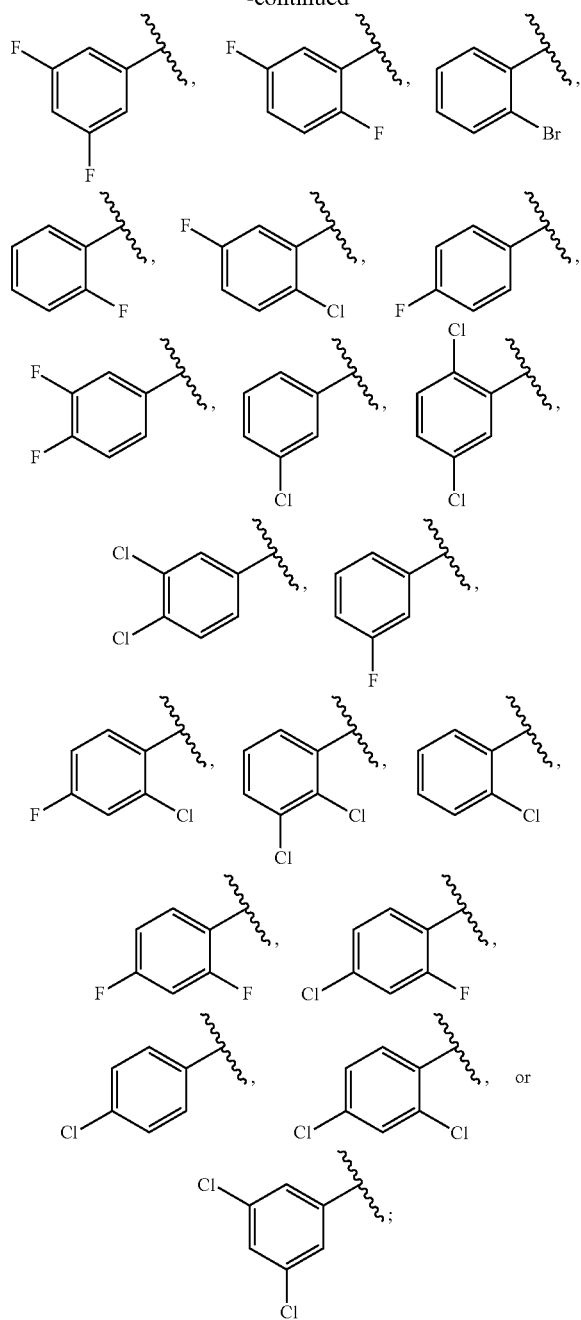

and $Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In certain aspects, the compound of formula (I), or a pharmaceutically acceptable salt thereof, is administered orally.

In certain aspects, the compound of formula (I), or a pharmaceutically acceptable salt thereof, is administered on days 1, 8, and 15 of each treatment cycle.

In certain aspects, the dosing schedule comprises about twenty-six treatment cycles.

In certain aspects, the compound of formula (I), or a pharmaceutically acceptable salt thereof, is administered at a first dose for at least four treatment cycles and a second dose for treatment cycles 5 through 26.

In certain aspects, the first dose is from about 1.5 mg/week to about 3.0 mg/week, and the second dose is from about 2.3 mg/week to about 4.0 mg/week for each of 3 weeks out of a 4 week treatment cycle.

In certain aspects, the first dose of this disclosure is about 3.0 mg/week and the second dose is about 4.0 mg/week, or the first dose is about 3.0 mg/week and the second dose is about 3.0 mg/week, or the first dose is about 2.3 mg/week and the second dose is about 3.0 mg/week, or the first dose is about 2.3 mg/week and the second is about 2.3 mg/week, or the first dose is about 1.5 mg/week and the second is about 2.3 mg/week, or the first dose is about 1.5 mg/week and the second is about 1.5 mg/week for each of 3 weeks out of a 4 week treatment cycle. In certain aspects, the first dose is about 3.0 mg/week and the second dose is about 4.0 mg/week for each of 3 weeks out of a 4 week treatment cycle In certain aspects, the first dose and the second dose are the same.

In certain aspects, the dosing schedule comprises up to about twenty-six treatment cycles and the compound of formula (I), or pharmaceutically acceptable salt thereof, is administered at about 3.0 mg/week from the first treatment cycle up to the twenty-sixth treatment cycle.

In certain aspects, the compound of formula (I) of this disclosure is a compound of formula (IV)

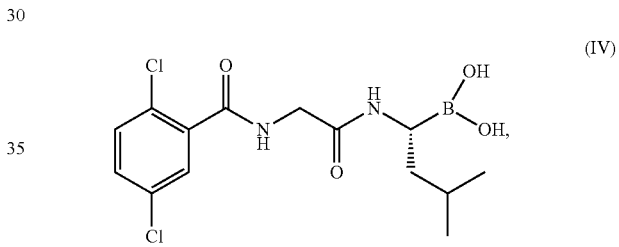

or an ester or a pharmaceutically acceptable salt thereof.

In certain aspects, the compound of formula (I) of this disclosure is a compound of formula (IIIa)

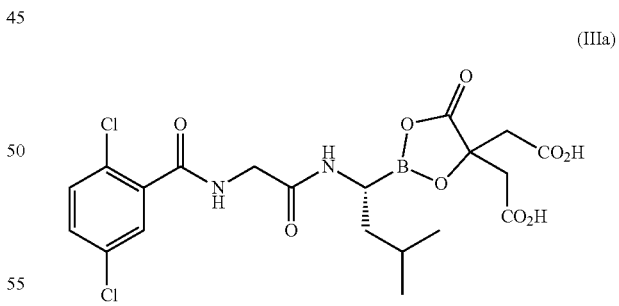

or a pharmaceutically acceptable salt thereof.

In certain aspects, the compound of formula (IV) is administered in the form of an ester.

In certain aspects, the compound of formula (IV) is administered in the form of the compound of formula (IIIa).

In certain aspects, the disclosure provides maintenance therapy comprising a proteasome inhibitor of formula (IIIa), or a pharmaceutically acceptable salt thereof, to treat cancer or prevent cancer recurrence or progression, wherein the cancer is a hematological malignancy.

In certain aspects, the disclosure provides maintenance therapy comprising a proteasome inhibitor of formula (IIIa), or a pharmaceutically acceptable salt thereof, to prevent progression of cancer in a cancer patient who has undergone a primary cancer, wherein the cancer is a hematological malignancy.

In certain aspects, the present disclosure provides maintenance therapies to prevent relapse or recurrence of multiple myeloma in a cancer patient who has undergone a primary cancer therapy.

In certain aspects, the present disclosure provides maintenance therapies to a cancer patient who has been diagnosed with multiple myeloma or refractory multiple myeloma.

In certain aspects, the present disclosure provides maintenance therapies to prevent progression of multiple myeloma in a cancer patient who has undergone a primary cancer therapy.

In certain aspects, the present disclosure provides maintenance therapies for treating a patient having, or at risk of developing or experiencing a recurrence of, a proteasome-mediated disorder.

In certain aspects, the present disclosure provides maintenance therapies for treating a patient having, or at risk of developing, or experiencing a recurrence of, a cancer selected from multiple myeloma.

In certain aspects, the present disclosure provides capsules comprising compound of formula (IIIa).

BRIEF DESCRIPTION OF FIGURES

FIG. 1 illustrates the results of exposure-response analyses of safety and efficacy data from patients with relapsed, refractory multiple myeloma enrolled in a phase 1 study.

FIG. 2 shows best overall response in 21 patients who received ixazomib maintenance therapy (n=21). The numbers on the bar refer to the percentage of the patients. Complete response (CR) or better was reached in 52 percent of patients. Very good partial response (VGPR) or better was reached in 71 percent of patients. Forty-eight percent of patients improved their response during maintenance, including two VGPR to near-CR (nCR), five VGPR to CR, one VGPR to stringent complete response (sCR), and two CR to sCR.

DETAILED DESCRIPTION OF THE INVENTION

The present disclosure provides various methods for treating cancer, or preventing cancer recurrence or progression. In the first aspect, the disclosure provides administering to a cancer patient a compound of formula (I), or a pharmaceutically acceptable salt thereof. In another aspect, the disclosure provides a dosing schedule of a compound of formula (I), or a pharmaceutically acceptable salt thereof, as a maintenance therapy to a patient who has undergone a primary cancer therapy and responded. In a further aspect, the disclosure provides maintenance therapy comprising a proteasome inhibitor of formula (IIIa), or a pharmaceutically acceptable salt thereof, to improve and maintain response for patients who have undergone a primary cancer therapy.

In another aspect, the disclosure provides maintenance therapy comprising a proteasome inhibitor of formula (IIIa), or a pharmaceutically acceptable salt thereof, to prevent patients from cancer recurrence or progression.

In another aspect, the disclosure provides maintenance therapy comprising a proteasome inhibitor of formula (IIIa), or a pharmaceutically acceptable salt thereof, to prevent cancer recurrence or progression.

In another aspect, the disclosure provides maintenance therapy comprising a proteasome inhibitor of formula (IIIa), or a pharmaceutically acceptable salt thereof, to treat cancer or prevent cancer recurrence or progression, wherein the cancer is a hematological malignancy.

In another aspect, the disclosure provides maintenance therapy comprising a proteasome inhibitor of formula (IIIa), or a pharmaceutically acceptable salt thereof, to treat, or prevent recurrence or progression of relapsed multiple myeloma.

In another aspect, the disclosure provides maintenance therapy comprising a proteasome inhibitor of formula (IIIa), or a pharmaceutically acceptable salt thereof, to treat, or prevent recurrence or progression of refractory multiple myeloma.

In another aspect, the disclosure provides maintenance therapy comprising a proteasome inhibitor of formula (IIIa), or a pharmaceutically acceptable salt thereof, to treat or prevent recurrence or progression of newly diagnosed multiple myeloma.

In another aspect, the disclosure provides maintenance therapy comprising a proteasome inhibitor of formula (IIIa) to prevent progression of newly diagnosed multiple myeloma.

In another aspect, the disclosure provides pharmaceutical compositions containing a proteasome inhibitor of formula (IIIa), or a pharmaceutically acceptable salt thereof.

In certain embodiments, the cancer is a hematological malignancy.

In certain embodiments, the hematological malignancy is multiple myeloma, mantle cell lymphoma, follicular cell lymphoma, T-cell lymphoma, peripheral T-cell lymphoma (PTCL), diffuse large B-cell lymphoma (DLBCL), or Waldenstrom's Macroglobulinemia.

In certain embodiments, the hematological malignancy is mantle cell lymphoma, follicular cell lymphoma, T-cell lymphoma, peripheral T-cell lymphoma (PTCL), diffuse large B-cell lymphoma (DLBCL), or Waldenstrom's Macroglobulinemia.

In certain embodiments, the hematological malignancy is amyloidosis. In certain embodiments, the hematological malignancy is systemic light chain amylodosis.

In certain embodiments, the cancer is newly diagnosed.
In certain embodiments, the cancer is relapsed.
In certain embodiments, the cancer is refractory.
In certain embodiments, the cancer is relapsed, or refractory multiple myeloma.
In certain embodiments, the cancer is newly diagnosed multiple myeloma.

Unless defined otherwise, all technical and scientific terms used herein have the same meaning as commonly understood by one of ordinary skill in the art to which this invention belongs. Accordingly, the following terms are intended to have the following meanings:

The term "maintenance therapy" refers to a therapeutic regimen that is designed to help a primary treatment succeed. For example, maintenance chemotherapy may be given to people who have a cancer in remission in an effort to prevent or delay a relapse, to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include low-intensity dosages as compared to dosages used for other types of therapies, for example, the primary therapy (i.e., the first line therapy, the induction therapy).

The term "primary therapy" refers to the initial treatment given to a patient based upon the diagnosis of the disease in the patient. The diagnosis of the disease may be the first occurrence of that disease in the patient, i.e., a newly diagnosed patient, or a reoccurrence of the disease in a patient, i.e., a relapsed patient. It is often part of a standard set of treatments, optionally, primary therapy include autologous stem cell transplant. When used by itself, primary therapy is the one accepted as the best treatment. If it doesn't cure the disease or it causes severe side effects, other treatment may be added or used instead. The term is also known to the person having ordinary skill in the art as first-line therapy when referring to the initial treatment of a newly diagnosed patient, or induction therapy, initial therapy, or primary treatment, each of which can refer to the initial treatment of a newly diagnosed patient or the initial treatment of a relapsed patient.

The term "induction therapy" refers to the first phase of treatment for cancer. The goal of induction therapy for multiple myeloma is to reduce the number of plasma cells in the bone marrow and the proteins that the plasma cells produce. Induction therapy may comprise three-four weeks as one treatment cycle.

The term "autologous stem cell transplant" refers to stem cells that are collected from an individual and given back to that same individual. A stem cell transplant is a procedure that is used in conjunction with high-dose chemotherapy, which is frequently more effective than conventional chemotherapy in destroying myeloma cells. Because high-dose chemotherapy also destroys normal blood-producing stem cells in the bone marrow, these cells must be replaced in order to restore blood cell production.

The term "low-intensity dose" refers to a reduced dose regimen in comparison with the dose regimen in the primary therapy. In certain embodiments, the proteasome inhibitor of formula (I) is reduced to a dose that is less than, 20%, 30%, 40%, 50%, 60%, 70%, of the dosing regimens in the primary therapies, for example the 5.5 mg dosage.

In certain embodiments, the reduced dosage is from about 3.0 mg to about 1.5 mg.

In certain embodiments, the reduced dosage is 3.0 mg, 2.3 mg, or 1.5 mg.

The term "survival" refers to the patient remaining alive, and includes progression-free survival (PFS) and overall survival (OS). Survival can be estimated by the Kaplan-Meier method, and any differences in survival are computed using the stratified log-rank test.

The term "progression-free survival (PFS)" refers to the time from treatment (or randomization) to first disease progression or death. For example it is the time that the patient remains alive, without return of the cancer (e.g., for a defined period of time such as about one month, two months, three months, three and a half months, four months, five months, six months, seven months, eight months, nine months, about one year, about two years, about three years, about five years, about 10 years, about 15 years, about 20 years, about 25 years, etc.) from initiation of treatment or from initial diagnosis. Progression-free survival can be assessed by Response Evaluation Criteria in Solid Tumors (RECIST).

The term "overall survival" refers to the patient remaining alive for a defined period of time (such as about one year, about two years, about three years, about four years, about five years, about 10 years, about 15 years, about 20 years, about 25 years, etc.) from initiation of treatment or from initial diagnosis.

The term "proteasome-mediated disorder" refers to any disorder, disease or condition which is caused or characterized by an increase in proteasome expression or activity, or which requires proteasome activity to sustain the condition. The term "proteasome-mediated disorder" also includes any disorder, disease or condition in which inhibition of proteasome activity is beneficial.

For example, compounds and pharmaceutical compositions of this disclosure are useful in treatment of disorders mediated via proteins (e.g., NFκB, $p27^{Kip}$, $p21^{WAF/CIP1}$, p53) which are regulated by proteasome activity such as cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors (hematologic malignancy). The term "cancer" encompasses diseases of skin, tissues, organs, bone, cartilage, blood, and vessels. The term "cancer" further encompasses primary and metastatic cancers.

Non-limiting examples of hematologic malignancies include amyloidosis, acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

The following pairs of phrases are interchangeable: a compound of formula (I) and a proteasome inhibitor of formula (I), a compound of formula (IIIa) and a proteasome inhibitor of formula (IIIa); and a compound of formula (IV) and a proteasome inhibitor of formula (IV).

For cancer therapy, efficacy may be measured by assessing the duration of survival, duration of progression-free survival (PFS), the response rates (RR) to treatments, duration of response, and/or quality of life.

Examples of the immunomodulatory drugs (immuno-modulating drugs) are thalidomide analogues. Examples of immunomodulating drugs include lenalidomide and pomalidomide.

Proteasome inhibitors are drugs that block the action of proteasomes, cellular complexes that break down proteins, like the p53 protein. Proteasome inhibitors are being studied in the treatment of cancer, especially multiple myeloma. Examples of proteasome inhibitors are bortezomib, carfilzomib, disulfiram, epigallocatechin-3-gallate, salinosporamid A, ONX0912, CEP-18770, and Epoxomicin.

Further examples of proteasome inhibitors are bortezomib, ixazomib, carfilzomib, disulfiram, epigallocatechin-3-gallate, salinosporamid A, ONX0912, CEP-18770, and Epoxomicin.

In certain embodiments, the proteasome inhibitor is bortezomib.

In certain embodiments, the proteasome inhibitor is ixazomib or ixazomib citrate.

In certain embodiments, the proteasome inhibitor is carfilzomib.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "comprises" refers to "includes, but is not limited to."

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of this disclosure can be manufactured by methods well known in the art such as conventional granulating, mixing, dissolving, encapsulating, lyophilizing, or emulsifying processes, among others. Compositions may be produced in various forms, including granules, precipitates, particulates, or powders.

The term "orally" refers to administering a composition that is intended to be ingested. Examples of oral forms include, but are not limited to, tablets, pills, capsules, powders, granules, solutions or suspensions, and drops. Such forms may be swallowed whole or may be in chewable form.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition such that they release the active ingredient(s) only, or preferentially, in a certain part of the intestinal tract, optionally, in a delayed manner. Examples of embedding compositions that can be used include polymeric substances and waxes.

In solid dosage forms the active ingredients may be mixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

The active ingredients can also be in micro-encapsulated form with one or more excipients as noted above.

The terms "boronate ester" and "boronic ester" are used interchangeably and refer to a chemical compound containing a —B($Z^1$)($Z^2$) moiety, wherein $Z^1$ and $Z^2$ together form a cyclic boronic ester having 2-20 carbon atoms, and optionally one or more heteroatoms selected from N, S, or O.

In certain embodiments, the proteasome inhibitor of formula (I) refers to the following formula:

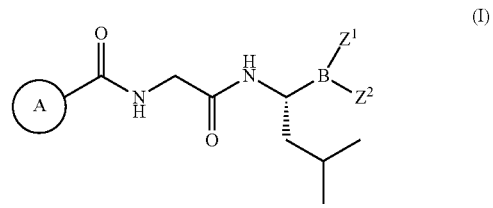

(I)

or a pharmaceutically acceptable salt, stereoisomeric or tautomeric form thereof, wherein ring A is

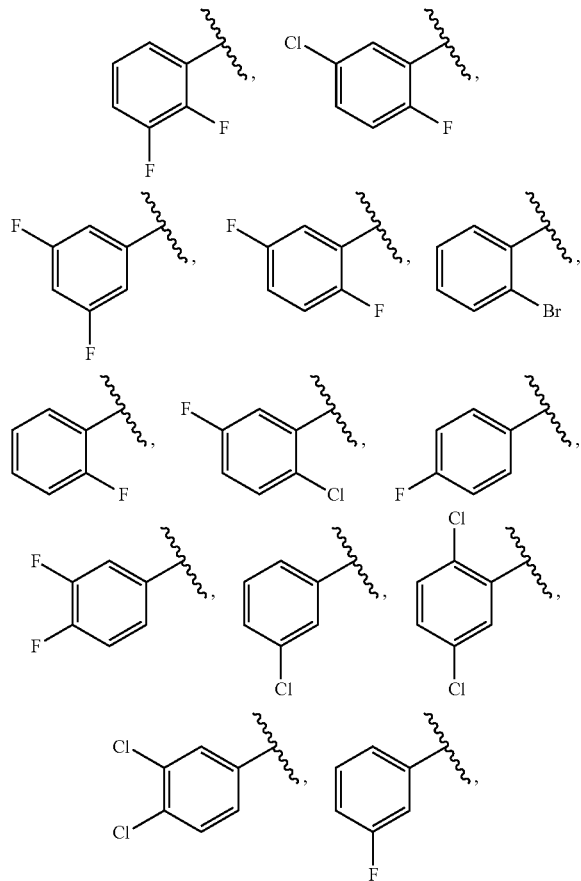

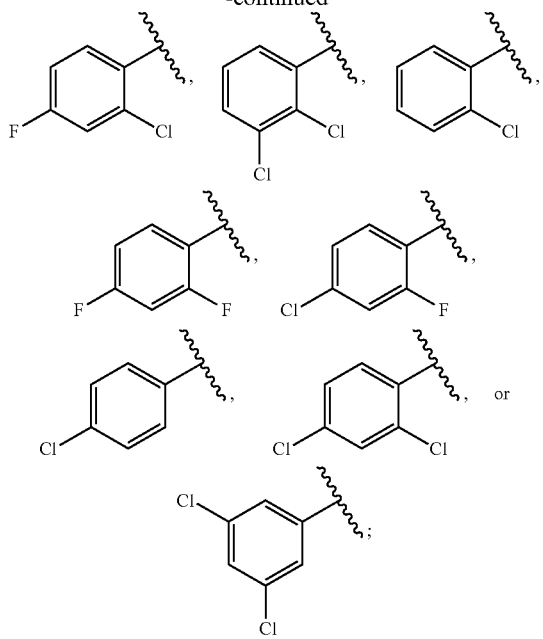

and
Z¹ and Z² are each independently hydroxyl; or Z¹ and Z² together form a cyclic boronic ester having 2-20 carbon atoms, and optionally one or more heteroatoms selected from N, S, or O.

In certain embodiments, the proteasome inhibitor of formula (I) is characterized by formula (Ia):

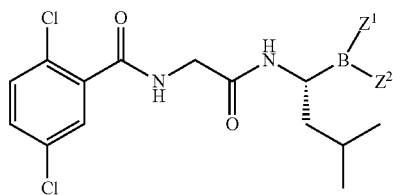

(Ia)

or a pharmaceutically acceptable salt, stereoisomeric or tautomeric form thereof, wherein: Z¹ and Z² are each independently hydroxyl; or Z¹ and Z² together form a cyclic boronic ester having 2-20 carbon atoms, and optionally one or more heteroatoms selected from N, S, or O.

In certain embodiments, the proteasome inhibitor of formula (I) is characterized by formula (II):

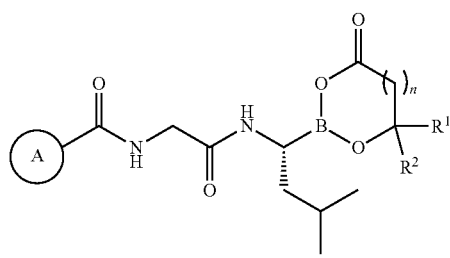

(II)

or a pharmaceutically acceptable salt, stereoisomeric or tautomeric form thereof, wherein: ring A is defined above; $R^1$ and $R^2$ independently is $-(CH_2)_p-CO_2H$; wherein one of carboxylic acids optionally forms a further bond with the boron atom; n is 0 or 1; and p is 0 or 1.

In certain embodiments, the proteasome inhibitor of formula (I) is characterized by formula (III):

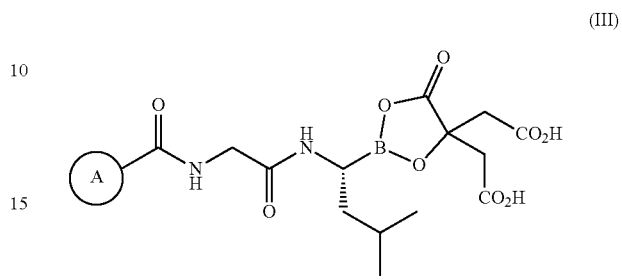

(III)

or a pharmaceutically acceptable salt, stereoisomeric or tautomeric form thereof, wherein ring A is defined above.

In one embodiment, the proteasome inhibitor of formula (I) is a compound of formula (IIIa):

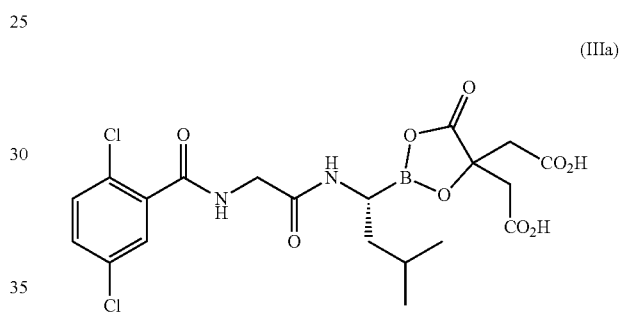

(IIIa)

or a pharmaceutically acceptable salt, stereoisomeric or tautomeric form thereof.

In one embodiment, the proteasome inhibitor of formula (IIIa) is in a substantially crystalline form.

In one embodiment, proteasome inhibitor formula (I) is a compound of formula (IV):

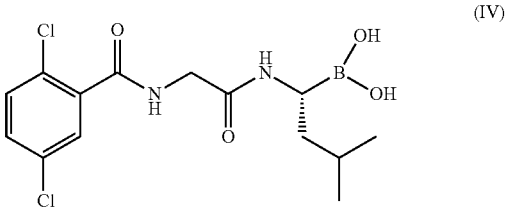 [SMILES: CC(C)C[C@H](NC(=O)CNC(=O)c1cc(Cl)ccc1Cl)B(O)O]

(IV)

or an ester or a pharmaceutically acceptable salt thereof.

Synthetic methods for the preparation of proteasome inhibitor of formulas (I), (II), (III), (IIIa) and (IV) are well known in the art, for example, described in U.S. Pat. Nos. 7,442,830, 7,687,662, 8,003,819, 8,530,694, and International Patent Publication WO 2009/154737, which are hereby incorporated by reference specifically and in their entirety.

The compound of formula (IV), also known as ixazomib, is a peptide boronic acid developed by Millennium Pharmaceuticals, Inc. Ixazomib is the biologically active molecule that potently, reversibly, and selectively inhibits the proteasome. The compound of formula (IIIa) is a citrate ester of ixazomib, referred to as ixazomib citrate herein. Ixazomib citrate rapidly hydrolyzes to ixazomib upon contact with either plasma or aqueous solutions. In contrast to the first-in-class, small molecule proteasome inhibitor bortezomib (VELCADE®), ixazomib demonstrates a faster dissociation rate from the proteasome, possibly resulting in enhanced tumor penetration, exhibits antitumor activity in a broader range of tumor xenografts, and has more prolonged tissue penetration.

Ixazomib preferentially binds the β5 site of the 20S proteasome with a concentration producing 50% inhibition ($IC_{50}$) of 3.4 nM. At higher concentrations, it also inhibits the activity of the β1 and β2 sites. Ixazomib is selective for the proteasome when tested against a panel of proteases ($IC_{50}$ values between 20 and 100 µM), kinases ($IC_{50}$ values>10 µM), and receptors ($IC_{50}$ values>10 µM). Ixazomib and bortezomib have different β5 proteasome dissociation half-lives ($t_{1/2}$), reflecting differences in their on-off binding kinetics (the β5 proteasome dissociation [$t_{1/2}$] for ixazomib citrate and bortezomib is 18 and 110 minutes, respectively). Kupperman E, et al. Cancer Res 2010; 70:1970-1980.

Ixazomib has been evaluated in clinical studies that have included patients with advanced solid tumors, lymphoma, relapsed/refractory multiple myeloma (RRMM), and relapsed or refractory light-chain (AL) amyloidosis and demonstrated early signs of activity. Data suggest a favorable toxicity profile with low rates of peripheral neuropathy (PN). Richardson P G, et al. Blood 2014; 124:1038-1046. Kumar S K, et al. Blood 2014; 124:1047-1055. Ongoing studies continue to investigate both single-agent ixazomib and ixazomib in combination with standard treatments. Additional clinical studies are evaluating ixazomib in combination with lenalidomide and dexamethasone (LenDex) versus placebo/LenDex at an ixazomib dose of 4 mg weekly. The emerging safety profile indicates that ixazomib is generally well tolerated. Kumar S, et al. Blood 2012; 119:4375-4382. Richardson P G, et al. Blood; 2010; 116:679-686. Jakubowiak A J, et al. Blood 2012; 120:1801-1809.

To select an appropriate dose for ixazomib maintenance study, Applicant conducted exposure-response analyses of safety and efficacy data from patients with relapsed, refractory multiple myeloma enrolled in a phase 1 study of weekly single-agent ixazomib. The analysis was designed to yield initial estimates of a biologically active exposure/dose range of ixazomib associated with disease control and acceptable tolerability, thereby ensuring adequate tolerability for long-term treatment while maintaining drug exposures in the biologically active range. The methods and results of these analyses are described below.

Exposure/Efficacy Analyses

Safety (S) and efficacy (E) data from patients enrolled in a phase 1 study of weekly single-agent ixazomib in relapsed and refractory multiple myeloma were used (N=44). The ixazomib dose range investigated was 1-8.9 mg. The metric of exposure (Ex) was AUC per day (derived from individual clearance values using population pharmacokinetics) for both exposure logistic regression analyses Ex/S and Ex/E. Ex/S analysis was done on seven adverse events (AEs): non-hematologic (non-H) (fatigue, rash, peripheral neuropathy, diarrhea) and hematologic (H) (anemia, thrombocytopenia, neutropenia). The non-hematologic adverse events data were categorized into grade≥2 vs. grade≤1 groups while hematologic adverse events data were grouped into grade≥3 vs. grade≤2. The data were categorized in this way as maintenance treatment should have a tolerable adverse events profile and contribute to acceptable quality of life. Different cut-offs were used for hematologic and non-hematologic adverse events because grade 3 hematologic adverse events may have less impact on quality of life and be more manageable than grade 2 non-hematologic adverse events such as diarrhea. For exposure efficacy (Ex/E), data were categorized as: ≥stable disease (SD) vs. progressive disease (PD). Clinical benefit rate including SD achieved in relapsed or refractory patients may be a meaningful predictor of expected response in a maintenance setting. The logistic regression analyses were done using SPLUS software version 8.1.

Results of the logistic regression analyses indicated that of the 7 evaluated AEs, statistically significant relationships to Ex ($p<0.05$) were observed for 5 AEs (fatigue, rash, diarrhea, thrombocytopenia, neutropenia) and clinical benefit rate (≥SD). At a starting dose of 3.0 mg weekly (54% of MTD), the model predicts ~33% ≥SD, and incidence of grade≥2 non-H AEs (rash 16%, diarrhea 19% and fatigue 19%) and grade≥3 H AEs (neutropenia 10%, thrombocytopenia 22%). Further, the 3.0 mg dose is within the therapeutic range and represents one dose level below the starting dose used in ongoing phase 3 trials in relapsed, refractory and previously untreated multiple myeloma patients.

FIG. 1 illustrates the relationship of patients' exposure to response (clinical benefit and safety) of ixazomib dose. FIG. 1 indicates that a favorable benefit versus risk may be achieved at weekly doses of 3.0 mg and 4.0 mg, below the maximum tolerated dose. Therefore, in the maintenance therapy, patients may initiate ixazomib at a once-weekly dose of 3.0 mg, increased to 4.0 mg if acceptable tolerability is determined after four cycles, to provide maximum clinical benefit.

Maintenance Therapy

Maintenance therapy is a long-duration therapy intended to prolong the duration of a patient's response to the primary treatment. Long-term maintenance therapy improves survival outcomes, including progression-free survival and sometime overall survival, in both the transplant and non-transplant settings. However, agents for continuous therapy need to be convenient and well tolerated. The balance of benefit versus risk is paramount in the maintenance therapy. Requirements for a successful maintenance therapy include good long-term tolerability and adherence (low discontinuation rates due to toxicity and convenience of administration), demonstration of clinical benefit either in prolonging survival or improving quality of life without shortening survival, and a favorable benefit to risk ratio. Although there is emerging evidence for the clinical benefit of maintenance therapy following stem cell transplant/therapy, a positive benefit and risk balance is yet to be established in existing therapies. There are to date no drugs approved for maintenance in patients with newly diagnosed multiple myeloma and patients with relapsed, refractory multiple myeloma.

In one embodiment, the maintenance therapy of this disclosure comprises administering a compound of formula (IIIa) (ixazomib citrate) to patients with newly diagnosed multiple myeloma, wherein the patients have already undergone induction therapy and a single autologous stem cell transplant.

In one embodiment, the maintenance therapy of this disclosure comprises administering a compound of formula (IIIa) (ixazomib citrate) to patients with newly diagnosed multiple myeloma, wherein the patients have already undergone induction therapy and one or more autologous stem cell transplants.

In one embodiment, the maintenance therapy of this disclosure comprises administering a compound of formula (IIIa) (ixazomib citrate) to patients with newly diagnosed multiple myeloma, wherein the patients have already undergone induction therapy according to regional standard of care, followed by a conditioning regimen containing high-dose therapy such as melphalan (200 mg/m$^2$) and a single autologous stem cell transplant. Induction therapy must include proteasome inhibitor and/or immunomodulating drugs-based regimens.

In certain embodiments, the induction therapy includes a proteasome inhibitor, wherein the proteasome inhibitor is ixazomib or ixazomib citrate.

In one embodiment, the maintenance therapy of this disclosure comprises administering a compound of formula (IIIa) (ixazomib citrate) to patients with newly diagnosed multiple myeloma wherein the patients have already undergone induction therapy and have not undergone autologous stem cell transplant.

In certain embodiments, patients who have achieved clinical and hematologic recovery following induction therapy, high-dose therapy, and autologous stem cell transplant will initiate screening for the maintenance therapy eligibility no earlier than 75 days after transplant, complete screening within 15 days, and be randomized no later than 115 days after transplant. Eligible patients (those who have a documented complete response, very good partial response, or partial response to induction therapy during screening) may be treated with ixazomib maintenance therapy. The stratification factors, induction regimen (proteasome inhibitors without immunomodulating drugs, immunomodulating drugs without proteasome inhibitors, or proteasome inhibitors and immunomodulating drugs); pre-induction International Staging System (ISS) (stage 1 vs. stage 2 or 3); and response after transplantation, defined as the response following induction therapy, high-dose therapy, and autologous stem cell transplant measured during screening (complete response, very good partial response, or partial response).

In certain embodiments, patients with newly diagnosed multiple myeloma who have had a response (complete response, very good partial response, or partial response) to induction therapy followed by high-dose therapy and autologous stem cell transplant may be treated with ixazomib maintenance therapy.

In certain embodiments, patients with newly diagnosed multiple myeloma who have had a response (complete response, very good partial response, or partial response) to induction therapy followed by autologous stem cell transplant may be treated with ixazomib maintenance therapy.

In certain embodiments, patients with newly diagnosed multiple myeloma who have had a response (complete response, very good partial response, or partial response) to induction therapy and who have not undergone stem-cell transplant may be treated with ixazomib maintenance therapy.

In certain embodiments, the maintenance therapy of this disclosure comprises administering a compound of formula (IIIa) (ixazomib citrate) to patients with a hematological malignancy wherein the patients have already undergone induction therapy.

In certain embodiment, the maintenance therapy of this disclosure comprises administering a compound of formula (IIIa) (ixazomib citrate) to patients with a hematological malignancy, wherein the patients have already undergone induction therapy and one or more autologous stem cell transplants In certain embodiment, the maintenance therapy of this disclosure comprises administering a compound of formula (IIIa) (ixazomib citrate) to patients with a hematological malignancy, wherein the patients have already undergone induction therapy and have not undergone autologous stem cell transplant.

In certain embodiments, the induction therapy comprises a chemotherapeutic regimen. Examples of such chemotherapeutic regimen include but are not limited to, CHOP (cyclophosphamide, doxorubicin, vincristine, and prednisone), R-CHOP (rituximab, cyclophosphamide, doxorubicin, vincristine, and prednisone), R-EPOCH (etoposide, rituximab, cyclophosphamide, doxorubicin, vincristine, and prednisone), HyperCVAD (cyclophosphamide, vincristine, doxorubicin, dexamethasone alternating with methotrexate and cytarabine) with or without rituximab, or VAD (vincristine, doxorubicin, dexamethasone).

In certain embodiments, the induction therapy comprises proteasome inhibitor and/or immunomodulating drugs-based regimens.

In certain embodiments, patients are administered with ixazomib citrate capsule orally once-a-week for three consecutive weeks followed by one week without the capsule. This four-week (28-day) dosing regimen comprises one treatment cycle. In certain embodiments, patients are administered ixazomib citrate capsules once on days 1, 8, and 15 in a 28-day cycle.

In certain embodiments, the proteasome inhibitor of formula (I), or a pharmaceutically acceptable salt thereof, is administered at a first dose for at least four treatment cycles and a second dose in the treatment cycles 5 through 26.

In one embodiment, the first dose strength of 3.0 mg/week of ixazomib in the form of ixazomib citrate capsule will be used for patients from the first treatment cycle through the fourth treatment cycle. Upon evaluation of toxicities at the completion of the fourth treatment cycle, patients will receive a second dose strength of ixazomib at an increased dose strength of 4.0 mg/week beginning with the fifth treatment cycle through the twenty-sixth treatment cycle, and administered on the same schedule of the treatment cycles 1-4 for the duration of the maintenance therapy, to provide maximum possible clinical benefit for patients who tolerated the first four cycles of treatment.

In one embodiment, the first dose strength of ixazomib in the form of ixazomib citrate capsule will be used for patients starting from the first treatment cycle. If the patient is tolerating the first dose strength, the patient may receive a second dose at an increased dose strength at any time upon evaluation of toxicities after the first dose.

In one embodiment, the first dose strength of 3.0 mg/week of ixazomib in the form of ixazomib citrate capsule will be used for patients starting from the first treatment cycle. If the patient is tolerating the 3.0 mg/week of dose strength, the patient may receive a second dose at an increased dose strength of 4.0 mg/week at any time upon evaluation of toxicities after the first dose.

In one embodiment, the first dose strength of 4.0 mg/week of ixazomib in the form of ixazomib citrate capsule will be used for patients starting from the first treatment cycle. If the patient is tolerating the 4.0 mg/week of dose strength, the patient may continue at the 4.0 mg/week dose strength.

In one embodiment, the first dose of 3.0 mg of ixazomib in the form of ixazomib citrate capsule will be used for patients from the first treatment cycle through the fourth treatment cycle. Upon evaluation of toxicities at the completion of the fourth treatment cycle, patients who would not tolerate the increased dose strength will remain at the starting dose strength of 3.0 mg/week for the fifth treatment cycle through the twenty-sixth treatment cycle, and administered on the same schedule of the treatment cycles 1-4 for the duration of the maintenance therapy.

In certain embodiments, patients experiencing adverse events during any treatment cycle may continue in the maintenance therapy, but may have ixazomib doses held or reduced by at least 1 dose level. In certain embodiments, the reduced doses are from about 3.0 mg to about 1.5 mg. In certain embodiments, the reduced doses are 3.0 mg, 2.3 mg, and 2.5 mg.

The treatment period of the maintenance therapy is defined as any time a patient is receiving the proteasome inhibitor of formula (I) of this disclosure and will comprise 28-day treatment cycles. In certain embodiments, patients will have treatment assessments performed at regular treatment cycle intervals while they are participating in the therapy: weekly (days 1, 8, and 15) for the first cycle, twice a treatment cycle during the second cycle (days 1 and 8), and then once a treatment cycle for the remainder of their participation in the treatment period, until they experience progressive disease or discontinue for alternate reasons.

In certain embodiments, patients will be assessed for disease response and progression, according to the International Myeloma Working Group criteria, every cycle during the treatment period and subsequently every four weeks during the progression-free survival on maintenance therapy or before the next line of therapy if discontinued before the progression follow-up period until progressive disease. Following progressive disease, patients will be followed in the overall survival follow-up period. Patients will initially be followed every four weeks until initiation of the next line of therapy by the treating physician. All patients will then be followed every 12 weeks until death or termination of the therapy. During the overall survival follow-up period, patients and their treating physician will be contacted for evaluation of the next line of therapy, Health-related quality of life (only until initiation of the next line of therapy), disease status, and survival. Health-related quality of life (HRQL) will be evaluated through patient self-reported instruments, from randomization to the time of initiation of the next line of therapy. After progression and following initiation of the next line of therapy, determination of disease response and progression will be assessed by the treating physician according to International Myeloma Working Group criteria.

In certain embodiments, adverse events will be assessed, and laboratory values, vital signs, and electrocardiograms (ECGs) will be obtained to evaluate the safety and tolerability of ixazomib. Toxicity will be evaluated according to National Cancer Institute Common Terminology Criteria for Adverse Events (NCI CTCAE), version 4.03, effective date 14 Jun. 2010.

In certain embodiments, therapeutic efficacy will be measured. A measured change in the patient between an earlier time point and a subsequent time point indicates that the maintenance therapy is therapeutically effective.

In certain embodiments, the first point may be, for example, prior to administration, after the first day of administration, after the fifth day of administration, at the beginning of a treatment cycle, at the end of a treatment cycle, etc. Regardless of when the first time point is, the second time point is subsequent to the first time point.

During the course of treatment, patient data may be collected and used to assess the efficacy of treatment. The relevant data include pharmacokinetic(s) data.

In certain embodiments, patients will receive maintenance therapy for a maximum duration of approximately 24 months (26 cycles, to the nearest complete cycle), or until documented disease progression (on the basis of the International Myeloma Working Group criteria) or intolerable toxicities, whichever comes first.

In certain embodiments, patients will receive maintenance therapy for approximately 24 months. In certain embodiments, patients will receive maintenance therapy until documented disease progression (on the basis of the International Myeloma Working Group criteria) or intolerable toxicities. In certain embodiments, patients will receive maintenance therapy for as long as it is clinically indicated (beyond 26 cycles).

In certain embodiments, patients who complete 24 months of treatment cycles, clinical, laboratory, response, and Health-related quality of life with an emphasis on tolerability and symptom burden, as well as minimal residual disease assessments, will be made. Following documented disease progression, subsequent therapy will be determined by the treating physician.

In certain embodiments, adult patients age 18 years or older with a confirmed diagnosis of multiple myeloma who have had a response (complete response, very good partial response, or partial response) to primary multiple myeloma therapy consisting of standard of care induction, a conditioning regimen containing high-dose melphalan (200 mg/m$^2$), and single autologous stem cell transplant will be eligible for the maintenance therapy.

In certain embodiments, patients who meet the following criteria may receive the maintenance therapy:
  a. Adult male or female patients 18 years or older with a confirmed diagnosis of symptomatic multiple myeloma.
  b. Documented results of cytogenetics/fluorescence in situ hybridization (FISH) obtained at any time before transplant, and International Staging System staging at the time of diagnosis if available.
  c. Underwent standard of care induction therapy/primary therapy (the therapy must include proteasome inhibitor and/or immunomodulating drugs-based regimens as primary therapy for multiple myeloma), followed by a single autologous stem cell transplant with a high-dose melphalan (200 mg/m$^2$) conditioning regimen, within 12 months of diagnosis.
  d. Started screening no earlier than 75 days after transplant, completed screening within 15 days, and randomized no later than 115 days after transplant.
  e. Patient may not receive post-autologous stem cell transplant consolidation therapy.
  f. Response to autologous stem cell transplant (partial response, very good partial response, complete response/stringent complete response).
  g. Eastern Cooperative Oncology Group performance status of 0 to 2.

In certain embodiments, patients who meet the following criteria may receive the maintenance therapy:
  a. Adult male or female patients 18 years or older with a confirmed diagnosis of symptomatic newly diagnosed multiple myeloma according to standard criteria.
  b. Completed six to 12 months (±two weeks) of initial therapy, during which the patient was treated to best response, defined as the best response maintained for two cycles after the M-protein nadir is reached.
  c. Documented major response (partial response, very good partial response, complete response according to the International Myeloma Working Group (IMWG) uniform response criteria, version 2011, after the initial therapy).

In certain embodiments, active ixazomib is provided to patients in strengths of 4.0 mg, 3.0 mg, 2.3 mg, and 1.5 mg.

In certain embodiments, ixazomib is administrated to the patients as ixazomib citrate in solid dose capsules.

In certain embodiments, ixazomib citrate capsules in the maintenance therapy contain various dose strengths, including 0.5 mg, 2.3 mg, 3.0 mg, or 4.0 mg of ixazomib. The pharmaceutical compositions containing ixazomib citrate and pharmaceutically acceptable carriers of this disclosure can be manufactured by methods well known in the art, for example, described in International Patent Publication WO 2009/154737, which is hereby incorporated by reference specifically and in their entirety.

In certain embodiments, the ixazomib citrate capsules contain a mixture of ixazomib citrate, microcrystalline cellulose, talc, and magnesium stearate.

Tables 1A, 1B, 1C and 2 provide certain embodiments of ixazomib citrate capsules.

Dose strengths per capsule at the top of the Tables refer to the equivalent of ixazomib when it is hydrolyzed from ixazomib citrate upon contact with either plasma or aqueous solutions. For example, a 0.5 mg capsule refers to a capsule that contains the equivalent of 0.5 mg ixazomib per capsule. A 2.0 mg capsule refers to a capsule that contains the equivalent of 2.0 mg ixazomib per capsule. A 2.3 mg capsule refers to a capsule that contains the equivalent of 2.3 mg ixazomib per capsule. A 3.0 mg capsule refers to a capsule that contains the equivalent of 3.0 mg ixazomib per capsule. A 4.0 mg capsule refers to a capsule that contains the equivalent of 4.0 mg ixazomib per capsule. A 5.0 mg capsule refers to a capsule that contains the equivalent of 5.0 mg ixazomib per capsule.

TABLE 1A

Composition of the 2.3 mg Ixazomib Citrate Capsules

| Components | mg per Capsule | % per Capsule |
|---|---|---|
| Ixazomib citrate | 3.29* | 4.71 |
| Microcrystalline cellulose | 65.66 | 93.79 |
| Talc | 0.70 | 1.00 |
| Magnesium stearate | 0.35 | 0.50 |
| Total weight | 70.00 | 100.00 |

*The amount of ixazomib citrate is equivalent to 2.3 mg ixazomib.

TABLE 1B

Composition of the 3.0 mg Ixazomib Citrate Capsules

| Components | mg per Capsule | % per Capsule |
|---|---|---|
| Ixazomib citrate | 4.30* | 6.14 |
| Microcrystaltine cellulose | 64.65 | 92.36 |
| Talc | 0.70 | 1.00 |
| Magnesium stearate | 0.35 | 0.50 |
| Total weight | 70.00 | 100.00 |

*The amount of ixazomib citrate is equivalent to 3.0 mg ixazomib.

TABLE 1C

Composition of the 4.0 mg Ixazomib Citrate Capsules

| Components | mg per Capsule | % per Capsule |
|---|---|---|
| Ixazomib citrate | 5.73* | 5.0 |
| Microcrystalline cellulose | 107.5 | 93.5 |

TABLE 1C-continued

Composition of the 4.0 mg Ixazomib Citrate Capsules

| Components | mg per Capsule | % per Capsule |
|---|---|---|
| Talc | 1.15 | 1.00 |
| Magnesium stearate | 0.58 | 0.50 |
| Total weight | 115.00 | 100.00 |

*The amount of ixazomib citrate is equivalent to 4.0 mg ixazomib.

TABLE 2

Compositions of 0.5 mg Ixazomib Citrate Capsules

| Components | mg per Capsule |
|---|---|
| Ixazomib citrate | 0.72* |
| Microcrystalline cellulose | 102.70 |
| Talc | 1.05 |
| Magnesium stearate | 0.53 |
| Total weight (mg) | 105.00 |

*The amount of ixazomib citrate is equivalent to 0.5 mg ixazomib.

In certain embodiments, a single first dose of ixazomib is administrated orally to the patients weekly on days 1, 8, and 15 for three weeks, followed by one week without ixazomib in a 28-day cycle. Following the first four cycles of the 28-day cycle therapy, a second dose of ixazomib is administrated to the patients weekly on days 1, 8, and 15 for cycle 5 through cycle 26.

In certain embodiments, the first dose of ixazomib is 3.0 mg; the second dose of ixazomib is 4.0 mg.

In certain embodiments, the first dose of ixazomib is 3.0 mg; the second dose of ixazomib is 3.0 mg.

In certain embodiments, the first dose of ixazomib is 2.3 mg; the second dose of ixazomib is 3.0 mg.

In certain embodiments, the first dose of ixazomib is 2.3 mg; the second dose of ixazomib is 2.3 mg.

In certain embodiments, the first dose of ixazomib is 1.5 mg; the second dose of ixazomib is 2.3 mg.

In certain embodiments, the first dose of ixazomib is 1.5 mg; the second dose of ixazomib is 1.5 mg.

In certain embodiments, the maintenance therapy is initially given as a single, oral dose of 3.0 mg weekly on days 1, 8, and 15 for three weeks, followed by one week without ixazomib in a 28 day cycle. Following the first four cycles of therapy, the dose will be increased to 4.0 mg in cycle 5 through cycle 26 for patients tolerating the drug.

In certain embodiments, a single 3.0 mg dose of ixazomib is administrated orally to the patients weekly on days 1, 8, and 15 for 3 weeks, followed by one week without ixazomib in a 28-day cycle. Following the first four cycles of the 28-day cycle therapy, a second dose of 3.0 mg ixazomib is administrated to the patients weekly on days 1, 8, and 15 for cycle 5 through cycle 26.

In certain embodiments, a single 1.5 mg dose of ixazomib is administrated orally to the patients weekly on days 1, 8, and 15 for 3 weeks, followed by one week without ixazomib in a 28-day cycle. Following the first four cycles of the 28-day cycle therapy, a second dose of 2.3 mg ixazomib is administrated to the patients weekly on days 1, 8, and 15 for cycle 5 through cycle 26.

Clinical Study of Oral Single-Agent Ixazomib Maintenance Therapy

Twenty-one patients who completed the induction therapy received ixazomib maintenance therapy. During the induction therapy, patients received 4.0 mg ixazomib weekly on days 1, 8, 15; 25.0 mg lenalidomide on days 1-21, and 40 mg dexamethasone weekly on days 1, 8, 15, and 22, in a 28 day cycles.

These patients completed induction therapy and progressed to the maintenance phase. Sixteen patients entered at 4.0 mg ixazomib; four patients entered at 3.0 mg ixazomib; one patient entered at 2.4 mg ixazomib. The patients receiving the maintenance therapy have the characteristics shown in Table 3 and Table 4.

TABLE 3

| Patient Characteristics | Patients receiving maintenance, n = 21 |
|---|---|
| Median age, years (range) | 68 (34-77) |
| Age ≥65 years, n (%) | 12 (57) |
| Age ≥75 years, n (%) | 2 (10) |
| Male, n (%) | 13 (62) |
| White, n (%) | 16 (76) |
| ISS disease stage at diagnosis, n (%) | |
| I | 14 (67) |
| II | 7 (33) |
| III | 0 |
| MM subtype, n (%) | |
| IgG | 16 (76) |
| IgA | 3 (14) |
| IgD | 0 |
| Light chain | 2 (10) |
| Median creatinine clearance, ml/min | 83.5 |

TABLE 4

| Cytogenetics | Patients receiving maintenance, n = 21 |
|---|---|
| Patients with cytogenetic assessment, N* | 19 |
| Conventional/karyotype | 3 (16) |
| Molecular/FISH | 6 (32) |
| Both | 10 (53) |
| Unfavorable cytogenetics[†], n (%) | 3 (16) |
| Type of cytogenetic abnormality, n (%) | |
| del 13 (by metaphase cytogenetics) | 2 (11) |
| del 17 | 1 (5) |
| t(4; 14) | 0 |
| t(14; 16) | 1 (5) |
| 1q amplification | 0 |

*No sample collected for three patients.
[†]Unfavorable cytogentics includes del 17, t(4; 14), t(14; 16), and 1q amplification abnormalities detected by FISH or metaphase cytogenetics and del 13 detected by metaphase cytogenetics.

During the maintenance therapy phase, the patients received single agent ixazomib for a median of 19 treatment cycles (range 3-23), with a median treatment duration of 29.0 months (range 14.3-33.3). Table 5 shows the treatment exposure.

TABLE 5

| Median cycles of ixazomib received, n (range) at data cut-off | Patients receiving maintenance, n = 21 |
|---|---|
| Total (including induction and maintenance cycles) | 31 (15-35) |
| Maintenance cycles | 19 (3-23) |
| Median treatment duration, months (range) | 29.0 (14.3-33.3) |
| Maintenance duration, months (range) | 19.8 (2.3-22.9) |
| Mean relative dose intensity of ixazomib overall/during induction/during maintenance, % | 92/95/89.5 |
| Patients remaining on ixazomib maintenance, n (%) | 11 (52%) |

FIG. 2 shows best overall response in 21 patients who received ixazomib maintenance therapy (n=21).

The best response overall is: complete response (CR) or better was reached in 52(%) percent of patients (11/21) and very good partial response (VGPR) or better was reached in 71(%) percent of patients (15/21).

Forty-eight percent (48%) of patients improved their response during maintenance (10/21), including two VGPR to near-CR (nCR) (2/10), five VGPR to CR (5/10), one VGPR to stringent complete response (sCR) (1/10), and two CR to sCR (2/10). Median duration of response was 21.65 months (range 6.7-31.18).

Fifty-two percent (52%) of patients (11/21) remained on ixazomib maintenance after data cut-off of the study.

Median time to first response (≥rapid response "PR") was 0.99 months (range 0.92-5.78) and median time to best response was 7.46 months (range 1.02-24.74). Mean ixazomib relative dose intensity was 95 percent (95%) and 89.5 (89.5) percent in the induction and maintenance phases, respectively.

All patients who received ixazomib maintenance were alive after follow-up of 25.1-33.9 months.

We claim:

1. A method for delaying cancer recurrence or progression comprising orally administering to a patient, who has undergone a primary cancer therapy and who is in remission, a compound of formula (IV)

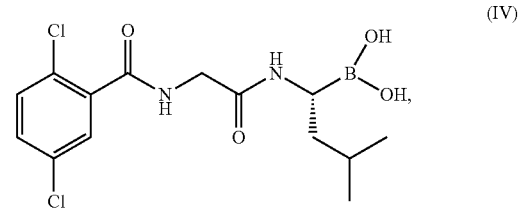 [SMILES: CC(C)C[C@H](NC(=O)CNC(=O)c1cc(Cl)ccc1Cl)B(O)O]

or an ester or a pharmaceutically acceptable salt thereof,
as a single-agent maintenance therapy on a dosing schedule comprising at least nineteen 28-day treatment cycles,
wherein the and up to the life span of the patient 28-day treatment cycle comprises four consecutive weeks in which the compound of formula (IV), or an ester or pharmaceutically acceptable salt thereof, is administered once a week for the first three weeks of the treatment cycle and the compound of formula (IV), or an ester or pharmaceutically acceptable salt thereof, is not administered during the fourth week.

2. The method of claim 1, wherein the dosing schedule comprises twenty-six treatment cycles.

3. The method of 1, wherein the compound of formula (IV), or an ester or pharmaceutically acceptable salt thereof, is administered at a first dose for at least four treatment cycles, and a second dose in the treatment cycles 5 through 26.

4. The method of claim 3, wherein the first dose is 3.0 mg and the second dose is 4.0 mg.

5. The method of claim 3, wherein the first dose is 3.0 mg and the second dose is 3.0 mg.

6. The method of claim 3, wherein the first dose is 2.3 mg and the second dose is 3.0 mg.

7. The method of claim 3, wherein the first dose is 2.3 mg and the second dose is 2.3 mg.

8. The method of claim 3, wherein the first dose is 4.0 mg and the second dose is 4.0 mg.

9. The method of claim 1, wherein said compound of formula (IV) is administered to the patient in a form of an ester, or a pharmaceutically acceptable salt thereof.

10. The method of claim 9, wherein the ester is a compound of formula (IIIa)

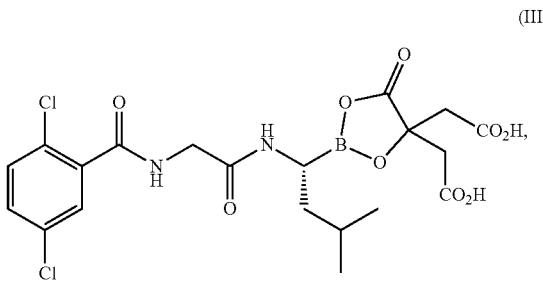

or a pharmaceutically acceptable salt thereof.

11. The method of claim 10, wherein the compound of formula (IIIa) is in a solid dosage form.

12. The method of claim 10, wherein the solid dosage form is capsule.

13. The method of claim 12, wherein the capsule comprises a mixture of the compound of formula (IIIa), microcrystalline cellulose, talc, and magnesium stearate.

14. The method of claim 1, wherein the primary cancer therapy comprises a proteasome inhibitor based regimen, or an immunomodulating drug based regimen, or both.

15. The method of claim 1, wherein the primary cancer therapy comprises an autologous stem cell transplant.

16. The method of claim 15, wherein the first 28-day treatment cycle begins at least 75 days after autologous stem cell transplant.

17. The method of claim 15, wherein the first 28-day treatment cycle begins prior to 115 days after autologous stem cell transplant.

18. The method of claim 1, wherein the primary cancer therapy comprises a proteasome inhibitor based regimen, or an immunomodulating drug based regimen, or both, followed by autologous stem cell transplant.

19. The method of claim 1, wherein the primary cancer therapy comprises a proteasome inhibitor based regimen, or an immunomodulating drug based regimen, or both, followed by a conditioning regimen comprising melphalan and autologous stem cell transplant.

20. The method of claim 19, wherein the proteasome inhibitor based regimen comprises bortezomib.

21. The method of claim 1, wherein the cancer is multiple myeloma or refractory multiple myeloma.

22. The method of claim 1, wherein the method is a maintenance therapy to delay relapse or recurrence of multiple myeloma in the patient who has undergone a primary cancer therapy.

23. The method of claim 1, wherein the method is a maintenance therapy to delay progression of multiple myeloma in the patient who has undergone a primary cancer therapy.

* * * * *